United States Patent [19]
Marquez et al.

[11] Patent Number: 5,453,550
[45] Date of Patent: Sep. 26, 1995

[54] PRODUCTION OF TAME FROM COKER NAPHTHA

[75] Inventors: Marco Marquez, Caracas; Raul Navarro, Miranda, both of Venezuela

[73] Assignee: Intevep, S.A., Caracas, Venezuela

[21] Appl. No.: 171,561

[22] Filed: Dec. 21, 1993

[51] Int. Cl.$^6$ .................................................... C07C 41/06
[52] U.S. Cl. ................................................................ 568/697
[58] Field of Search ............................................. 568/697

[56] References Cited

U.S. PATENT DOCUMENTS

| | | | |
|---|---|---|---|
| 5,238,541 | 8/1993 | Marquez et al. | 203/56 |
| 5,321,163 | 6/1994 | Hickey et al. | 568/697 |

OTHER PUBLICATIONS

Lange's, Handbook of Chemistry, 12th Ed. McGraw-Hill Book Company, New York, 1979, 9–175, 9–179.

Primary Examiner—Johann Richter
Assistant Examiner—John Peabody
Attorney, Agent, or Firm—Bachman & LaPointe

[57] ABSTRACT

A process for the production of alkyl tert alkyl ether, comprising the steps of providing a liquid hydrocarbon feedstock containing diolefin in an amount greater than or equal to about 2% wt, mixing said feedstock with an alcohol selected from the group consisting of methanol, ethanol, propanol and mixtures thereof and with hydrogen so as to provide a mixture of said feedstock, alcohol and hydrogen and contacting said mixture with an etherification catalyst under etherification process conditions including a pressure sufficient to maintain said hydrogen in a liquid phase, and a space velocity (LHSV) of less than or equal to about 1 $h^{-1}$ so as to provide said alkyl tert alkyl ether without poisoning said catalyst.

10 Claims, No Drawings

PRODUCTION OF TAME FROM COKER NAPHTHA

BACKGROUND OF THE INVENTION

The invention relates to the production of alkyl tert alkyl ethers and, specifically, to a process for producing tert amyl methyl ether (TAME) from a feedstock containing relatively high amounts of diolefin such as a light naphtha stream from a coker refinery facility.

Alkyl tert alkyl ethers are useful as fuel extenders and octane value improving agents in the production of unleaded gasoline. These ether additives are particularly useful as environmentally more acceptable substitutes for lead anti-knock compounds.

Of these ether additives, tert amyl methyl ether (TAME) is presently probably the most important oxygenate after methyl tert butyl ether (MTBE) and ethanol. TAME is produced from $C_5$ feedstocks from various refineries and petrochemical facilities. These feedstocks are a good source of isoamylene and are generally readily available, thereby rendering TAME further attractive economically. Additionally, TAME provides a reasonably good octane number while yielding a blend with a low RVP.

Main sources of isoamylene for TAME production include catalytic and steam cracker units. However, other feedstocks also provide a good supply of isoamylene. One such feedstock is a light naphtha cut from a typical coker unit. This feedstock has a similar amount of isoamylene to the aforementioned FCC and steam cracker $C_5$ cuts, but is generally worthless due to the relatively large degree of contaminants contained therein in the form of diolefins in the range of 5–6% wt, nitrogen compounds in the order of about 30 ppm and sulfur compounds in the range of about 2000 ppm or greater. Each of these contaminants tends to rapidly deactivate the etherification catalyst. In this regard, methods have been derived for negating the effects of the nitrogen compounds (see U.S. Pat. No. 5,238,541 to Marquez et al.) and sulfur (co-pending and commonly assigned U.S. patent application Ser. No. 08/128,383). However, no process has been provided for negating the adverse effect of diolefins and, accordingly, light coker naphtha feedstocks are not valued as etherification starting feedstocks.

It is therefore the primary object of the invention to provide a process for preparing alkyl tert alkyl ether from a feedstock having a relatively high level of diolefin wherein the catalyst is not poisoned.

It is a further object of the present invention to provide a process whereby TAME can be produced in an efficient, versatile and cost effective manner.

Other objects and advantages will appear hereinbelow.

SUMMARY OF THE INVENTION

In accordance with the present invention, the foregoing objects and advantages are readily obtained.

The present invention relates to a process for the production of an ether-rich additive from light hydrocarbon feedstocks and, more particularly, from light coker naphtha feedstocks having significant concentrations of diolefins. The feedstock is contacted with an etherification catalyst under etherification conditions sufficient to hydrogenate the diolefin so as to prevent the formation of gums from the diolefins which otherwise would foul and deactivate the catalyst.

The process of the present invention provides an economically attractive use for light coker naphtha feedstocks which provides TAME without rapid catalyst deactivation, thereby increasing process efficiency while at the same time decreasing processing costs.

DETAILED DESCRIPTION

The invention relates to a process for providing alkyl tert alkyl ether, especially tert amyl methyl ether (TAME) from feedstock having a relatively high diolefin content.

Processes for preparing alkyl tert alkyl ethers typically involve reacting a primary alcohol such as methanol with an olefin having a double bond on a tertiary carbon atom such as isobutylene, isoamylene or other desired isoalkenes. This reaction is typically carried out in the presence of a catalyst. Suitable known catalysts include Lewis acids (sulfuric acid) and organic acids (alkyl and aryl sulfonic acids). Particularly suitable are ion exchange resins in their acid form of the type marketed under the trademark "AMBERLIST 15" by Rohm and Haas, or Bayer product K2631.

When the feedstock to be treated has relatively high levels of diolefins, however, the ion exchange catalyst is rapidly deactivated. It is believed that the diolefins polymerize to form gums which foul the catalyst and deactivate it for further use in the etherification process. One high diolefin content feedstock is a light coker naphtha feedstock which typically contains a good amount of isoamylenes but which also has a relatively high level of diolefins. Such a feedstock may typically have a composition as follows:

| | |
|---|---|
| $C_4$ | 0–6% wt |
| iso-$C_5$ | 15–25% wt |
| Total $C_5$ | 85–95% wt |
| $C_6$ | 0–10% wt |
| Total $N_2$ | 0–20 ppm wt |
| nitrile | 0–19 ppm wt |
| diolefin | 2–7% wt |

According to the invention, such a feedstock is mixed with hydrogen and an alcohol selected from the group consisting of methanol, ethanol, propanol, and mixtures thereof, and contacted with a suitable etherification catalyst under etherification conditions so as to provide the desired ether-rich additive. In further accordance with the invention, the etherification process is carried out in a suitable reactor at a space velocity (LHSV) of less than about 10 $h^{-1}$, preferably between about 0.4 to about 1.0 $h^{-1}$, and most preferably about 0.6 $h^{-1}$. The process is also preferably carried out at a $H_2$/diolefin molar ratio of between about 2.0 to about 4.0, most preferably at about 3.8.

The temperature and pressure in accordance with the invention are selected so as to keep the gaseous hydrogen in the liquid hydrocarbon feedstock, thereby allowing the effective hydrogenation of diolefins in the feedstock so as to prevent catalyst deactivation. In this regard, the above mentioned relatively long residence time serves to further allow full hydrogenation as desired. The temperature is preferably maintained between about 60° C. to about 80° C. at the reactor inlet, more preferably at about 62° C., while the pressure is preferably maintained at about 22 bars. The foregoing process temperature and pressure provide an excellent rate of hydrogenation of the diolefins, up to about 99%, which substantially prevents gums from being formed and thereby protects the catalyst from rapid deactivation.

The process is also preferably carried out at a desired ratio of alcohol in the mixture to isoalkene in the feedstock. In accordance with the invention, the reaction is preferably carried out at an alcohol/isoalkene molar ratio of between about 1.0 to about 2.0.

In accordance with the foregoing, formerly useless feedstocks having diolefin contents greater than 2% and even up to about 7% by weight can be treated so as to provide valuable ether-rich additives such as TAME, without rapid catalyst deactivation. Diolefins are not allowed to polymerize during the reaction, so gums are not formed and the catalyst is not rapidly deactivated.

According to a further embodiment of the invention, if the feedstock contains significant levels of nitrogen compounds such as nitriles, the alcohol feedstock mixture may be distilled under controlled conditions so as to provide a hydrocarbon-alcohol azeotrope feedstock rich in $C_5$ and substantially free of nitriles so as to further protect the catalyst from deactivation. The process disclosed in the above mentioned U.S. Pat. No. 5,238,541 may suitably be used to neutralize or remove nitrogen.

It is noted of course that the present process is useful for any feedstock which contains a significant level of diolefins. Particularly suitable feedstocks are rich in $C_4$-$C_{12}$ hydrocarbons, especially $C_5$ hydrocarbons preferably having a relatively large percentage of isoamylenes. Table 1 below compares the compositions of feedstock from an FCC process, a steam cracking process, and a coker naphtha process.

TABLE 1

| COMPONENTS (wt %) | FCC | STEAM CRACKING | COKER |
|---|---|---|---|
| $C_4$ | 3 | 4 | 6 |
| ISOAMYLENES | 22 | 22 | 21 |
| TOTAL $C_5$ | 92 | 91 | 89 |
| $C_6$ | 5 | 5 | 5 |
| CONTAMINANTS (ppm wt) | | | |
| TOTAL NITROGEN | 10 | 2 | 20 |
| NITRILES | 9 | <1 | 19 |
| BASIC NITROGEN | 1 | 1 | 1 |
| TOTAL SULFUR | 10 | 10 | 189 |
| MERCAPTAN | <1 | <1 | <1 |
| DIOLEFIN (wt %) | 1.5 | 1.5 | 6.1 |

As shown, coker naphtha streams contain a significantly larger amount of contaminants than either FCC or steam cracking streams. Because the light coker naphtha stream does contain a good amount of total $C_5$ and isoamylene, however, the process of the present invention is particularly useful in providing a use for such light coker naphtha streams. According to the process of the invention, TAME yield is optimized to about 54–60% in the first of two etherification reactors, with a global yield of 65–75% and diolefin conversion up to 99%.

EXAMPLE 1

This example demonstrates the poisoning effect of high diolefin levels on the etherification catalyst. The test was run on a depentanizer unit which was 8 meters tall and 5 cm in diameter and which had a glass unit with stainless steel packing equivalent to about 40 theoretical trays and a 16 l/h feed capacity. The high diolefin feedstock is a light coker naphtha (LKN) from the Lagoven Flexicoquer unit in the Amuary refinery (Venezuela).

In Case 1, a feedstock with a low diolefin content was used. In Case 2, a high diolefin LKN. Both feedstocks were treated to remove nitrile in accordance with the distillation step of the foregoing U.S. Pat. No. 5,238,541. The feedstocks of Case 1 and Case 2 were then contacted with an etherification catalyst under the following process conditions:

LHSV=1 $h^{-1}$ $H_2$/diolefin molar ratio=1.5

Reactor inlet T=50° C.

Pressure=22 bar

The results obtained for Case 1 and Case 2 are set forth below in Table 2.

TABLE 2

| | Case 1 | Case 2 |
|---|---|---|
| Diolefin in Feedstock | 1.5% wt | 6.1% wt |
| Diolefin Conversion | 100% | 77% |
| TAME yield | 54% | 44% |

As shown, conventional etherification process conditions are not suitable for use with a feedstock (Case 2) having a relatively high diolefin content.

Conversion of the diolefin in Case 2 was not complete, and TAME yield was low.

EXAMPLE 2

The same feedstock as in Case 2 of Example 1 (Diolefin= 6.1% wt) was then treated under the following process conditions:

LHSV- 0.6 $h^{-1}$ $H_2$/diolefin molar ratio=3.8

Reactor inlet T=62° C.

Pressure=22 bar

The process yielded 99% conversion of diolefins, thereby preventing same from forming gums and fouling the catalyst, and also provided a TAME yield of 54%.

It is believed that the pressure sufficient to keep gaseous hydrogen in liquid hydrocarbon feedstock, combined with relatively low LHSV and relatively high reactor inlet temperature help to achieve almost total diolefin conversion (99%) in the feedstock which avoids polymerization and gum formation which, as set forth above, tend to foul the catalyst.

Thus, in accordance with the present invention, a process is provided whereby normally worthless feedstocks having high diolefin content can be treated to provide valuable ether-rich additives such as TAME.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A process for the production of alkyl tert alkyl ether, comprising the steps of:

providing a liquid hydrocarbon feedstock containing diolefin in an amount greater than or equal to about 2% wt;

mixing said feedstock with an alcohol selected from the group consisting of methanol, ethanol, propanol and mixtures thereof and with hydrogen so as to provide a mixture of said feedstock, alcohol and gaseous hydrogen; and contacting said mixture with an etherification catalyst under etherification process conditions including a pressure sufficient to maintain said gaseous hydrogen in the liquid hydrocarbon feedstock, a space velocity (LHSV) of between about 0.4 to about 1.0 $h^{-1}$, and a $H_2$/diolefin molar ratio of between about 2 to about 4 so as to provide said alkyl tert alkyl ether without poisoning said catalyst.

2. A process according to claim 1, wherein said etherification process conditions include a temperature of between about 60° C. to about 80° C.

3. A process according to claim 2, wherein said etherification process conditions include a space velocity (LHSV) of about 0.6 $h^{-1}$, a $H_2$/diolefin molar ratio of about 3.8, a reactor inlet temperature of about 62° C. and a pressure of about 22 bars.

4. A process according to claim 1, wherein said feedstock contains isoalkenes and said alcohol and said feedstock are mixed so as to provide said mixture with a molar ratio of alcohol to isoalkene of between about 1.0 to about 2.0.

5. A process according to claim 1, wherein said feedstock contains diolefin in an amount of between about 2.0 to about 7.0% wt.

6. A process according to claim 1, wherein said feedstock is a coker naphtha hydrocarbon feedstock.

7. A process according to claim 6, wherein said feedstock is rich in $C_5$.

8. A process according to claim 1, wherein said feedstock has a composition as follows:

| | |
|---|---|
| $C_4$ | 0–6% wt |
| isoamylene | 15–25% wt |
| Total $C_5$ | 85–95% wt |
| $C_6$ | 0–10% wt |
| Total $N_2$ | 0–20 ppm wt |
| nitrile | 0–19 ppm wt |
| diolefin | 2–7% wt |

9. A process according to claim 1, wherein said feedstock includes nitriles, the process further including the steps of:

distilling said mixture under controlled conditions so as to provide a $C_5$ hydrocarbon-alcohol azeotrope feedstock rich in $C_5$ and substantially free of nitriles; and contacting said azeotrope feedstock with said etherification catalyst.

10. A process according to claim 1, wherein said feedstock is rich in $C_5$ and wherein said alcohol is methanol, whereby said contacting step provides tert amyl methyl ethers (TAME).

* * * * *